United States Patent [19]
Bulteau et al.

[11] 3,975,434
[45] Aug. 17, 1976

[54] PROCESSES OF PRODUCING 2,5-DISUBSTITUTED BENZAMIDES

[75] Inventors: Gerard Bulteau, Paris; Jacques Acher, Itteville; Jean-Claude Monier, Lardy, all of France

[73] Assignee: Societe d'Etudes Scientifiques et Industrielles de l'Ile-de-France, Paris, France

[22] Filed: Sept. 23, 1974

[21] Appl. No.: 508,536

[30] Foreign Application Priority Data
Sept. 25, 1973  France .............................. 73.34436

[52] U.S. Cl. ..................... 260/556 B; 260/247.1 R; 260/268 R; 260/293.73; 260/309.7; 260/306.7 R; 260/326.47; 260/326.82; 260/559 T; 260/937; 424/321; 424/324
[51] Int. Cl.² ........................................ C07C 143/80
[58] Field of Search ......... 260/556 AR, 559 T, 937, 260/556 B, 556 C

[56] References Cited
FOREIGN PATENTS OR APPLICATIONS
884,206  12/1961  United Kingdom ............ 260/556 B OTHER PUBLICATIONS
Kodama et al., CA 78: 124313j (1/20/1973).
Kodama et al., CA 80: 95559c (12/15/1973).

*Primary Examiner*—Daniel E. Wyman
*Assistant Examiner*—Thomas A. Waltz
*Attorney, Agent, or Firm*—Frank M. Nolan

[57] ABSTRACT

2,5-Disubstituted benzamides are produced by an efficient, effective and economical method by the utilization of 4-methyl 2-chloro 1-3-2-dioxophosphorinane as a catalyst.

5 Claims, No Drawings

PROCESSES OF PRODUCING 2,5-DISUBSTITUTED BENZAMIDES

This invention relates to processes of producing 2,5-disubstituted benzamides, their acid addition salts and quaternary ammonium salts.

The 2,5-disubstituted benzamides of this invention have the following formula:

(I) 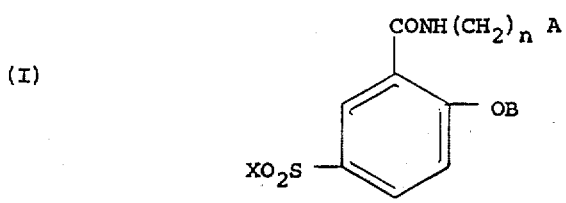

In formula I, B is alkyl of low molecular weight or alkenyl, both preferably having less than 5 carbon atoms; n is 1 or 2; and x is an amino, mono- or dialkylaino, alkyl or alkenyl, preferably of less than 5 carbon atoms. Examples of alkyl and alkenyl for B and X are methyl, ethyl, isopropyl, n-butyl, an allyl or a butenyl. The alkyl group of the alkylamino preferably has less than 5 carbon atoms such as ethyl, methyl, isopropyl or n-butyl.

In formula I, A is either a mono- or dialkylamino radical of low molecular weight or can be a heterocyclic radical having the formula;

(II) 

When A is a dialkylamino radical of low molecular weight, alkyl groups can be joined together to form a ring with or without nitrogen, oxygen or sulfur.

When the ring contains a nitrogen atom, the nitrogen atom can be joined to an alkyl group of low molecular weight, preferably less than 5 carbon atoms, such as methyl or n butyl. The resulting rings may be, for example, pyrrolidinyl, piperidinyl, imidazolidinyl, piperazino, morpholino and thiazolidinyl.

R is lower alkyl or alkenyl and m is an integer less than 4.

The alkyl of the mono- or dialkylamino radicals of A and the alkyl or alkenyl of B in formula I and the alkyl or alkenyl of R in formula II preferably have less than 5 carbon atoms, such as methyl, ethyl, isopropyl or allyl.

The 2,5-disubstituted benzamides which are produced in accordance with this invention are useful in the treatment of nervous disturbances.

The process of producing the 2,5-disubstituted benzamides in accordance with this invention comprises reacting a 2,5-disubstituted benzoic acid having the formula:

(III) 

with an amine having the formula:

(IV) $H_2N(CH_2)_n A$ 

in the presence of 4-methyl 2-chloro 1-3-2-dioxophosphorinane having the formula:

(V) 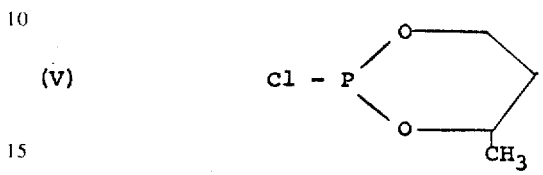

A, B, X, n of formulas III and IV have the same meaning as heretofore defined.

The 4-methyl 2-chloro 1-3-2-dioxophosphorinane may be prepared in accordance with the method described in Houben-Weyl, Methoden der Organischen Chemie, volume 12/2, page 49.

For obtaining an optimum result, the molecular proportion of the amine is of the order of 2½ times of the 2,5-disubstituted benzoic acid. Desirably, the 4-methyl 2-chloro 1-3-2-dioxophosphorinane present comprises a molecular equivalent plus about 10% excess of the 2,5-disubstituted benzoic acid. Preferably, the reaction is conducted in an inert solvent, such as dioxane. The 2,5-disubstituted benzoic acid and amine are mixed with an inert solvent, and then the mixture is agitated, after which the 4-methyl 2-chloro 1-3-2-dioxophosphorinane is added. The mixture is then heated for several hours under reflux. The solvent is removed by any suitable means such as evaporation. The resulting residue is dissolved in water and purified by conventional means, such as by crystallization.

The salts of addition, or quaternary ammonium salts of the 2,5-disubstituted benzamide may be prepared by conventional methods. Both acid addition salts and quaternary ammonium salts employed for use as medicaments should be pharmaceutically acceptable.

A more comprehensive understanding of this invention may be obtained by reference to the following examples.

EXAMPLE I

N-(1-ETHYL 2-PYRROLIDYLMETHYL) 2-METHOXY-5-SULFAMIDOBENZAMIDE 2.31 g (0.01 mol) of 2-methoxy-5-sulfamidobenzoic acid, 3.22 g (0.025 mol) of N-ethyl 2-aminomethylpyrrolidine and 50 ml of dioxan are placed in a 100 ml balloon flask provided with a stirrer and a condenser comprising a calcium chloride guard.

This mixture is stirred for 30 minutes. A yellowish gum is formed, and then 1.7 g (0.011 mol) of 4-methyl 2-chloro 1-3-2-dioxophosphorinane is added, and the mixture is heated for 5 hours under reflux. Cooling is effected, followed by evaporation of the solvent under vacuum. The residue is dissolved in 30 ml of water and 10 ml of ammonia is added. A light precipitate is filtered. The filtrate is raised to boiling temperature, then allowed to crystallize by cooling. Filtration is effected, then the product is washed with water and dried in a drying oven at 50°C.

-ethyl 2 g(yield: 59%) of N-(1ethyl 2-pyrrolidyl-methyl) 2-methoxy-5-sulfamidobenzamide (melting point: 179°C) is produced.

EXAMPLE II

N-(DIETHYLAMINOETHYL) 2-METHOXY 5-METHYLSULFONYLBENZAMIDE 2.3 g (0.01 mol) of 2-methoxy 5-methylsulfonylbenzoic acid, 2.9 g (0.025 mol) of N,N-diethyl ethylenediamine and 40 ml of dioxan are placed in a 100 ml balloon flask provided with a stirrer and a condenser.

This mixture is stirred for 30 minutes at room temperature, and then 1.7 g (0.011 mol) of 4-methyl 2-chloro 1-3-2-dioxophosphorinane is added. This mixture is heated for five hours under reflux, followed by cooling. The solvent is then evaporated under vacuum, 40 ml of water is added to the residue, and the product is precipitated by alkalizing the solution with sodium hydroxide. It is left to crystallize, followed by filtration, then washing with water. The crystals are dried in a drying oven at 50°C.

2.6 g (yield: 79%) of N-(diethylaminoethyl) 2-methoxy 5-methyl-sulfonylbenzamide (melting point: 117°C) is produced.

EXAMPLE III

N-(1-ETHYL 2-PYRROLIDYLMETHYL 2-methoxy 5-ETHYLSULFONYLBENZAMIDE 2.44 g (0.01 mol) of 2-methoxy 5-ethylsulfonylbenzoic acid, 3.22 g (0.025 mol) of N-ethyl 2-aminomethylpyrrolidine and 50 ml of dioxan are placed in a 100 ml balloon flask provided with a stirrer and a condenser upon which is mounted a calcium chloride guard.

The mixture is stirred for 30 minutes at room temperature, then 1.7 g (0.011 mol) of 4-methyl 2-chloro 1-3-2-dioxophosphorinane is added. The mixture is heated for five hours under reflux, followed by cooling. The solvent is evaporated under vacuum, then 50 ml of water is added to the residue and the solution is alkalized with sodium hydroxide. The solution is extracted 3 times with 25 ml of methylene chloride, and then the organic solution is dried with magnesium sulfate, and filtered, and the solvent is evaporated under vacuum. The residue is dissolved in acetone, and the solution is acidified with hydrochloric acid. The solution is left to crystallize in a cooler, followed by filtering and drying in a drying oven at 50°C. The product is recrystallized from a minimum amount of ethanol. 2.5 g (yield: 61%) of N-(1-ethyl 2-pyrrolidylmethyl) 2-methoxy 5-ethylsulfonylbenzamide hydrochloride (melting point: 190°C) is produced.

What we claim is:

1. The process of producing a 2,5-disubstituted benzamide, its acid addition salts and quaternary ammonium salts, said benzamide having the formula:

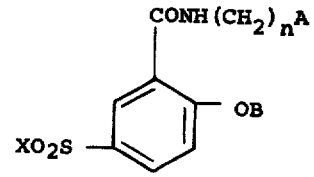

which comprises reacting in an inert solvent and at reflux temperature in the presence of a catalytic amount of 4-methyl 2-chloro 1-3-2-dioxophosphorinane a 2,5-disubstituted benzoic acid having the formula:

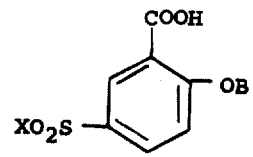

with an amine having the formula:

$H_2N(CH_2)_nA$ in which $n$ is 1 or 2; B is alkyl having less than 5 carbon atoms or alkenyl having less than 5 carbon atoms, X is amino, monoalkylamino, dialkylamino, alkyl or alkenyl, the alkyl group of each of which has less than 5 carbon atoms, and A is a mono- or dialkylamino radical the alkyl group of which has less than 5 carbon atoms, the molecular ratio of said 2,5-disubstituted benzoic acid to said amine being 1 to about 2.5.

2. The process of producing a 2,5-disubstituted benzamide in accordance with claim 1 in which the 2,5-disubstituted benzoic acid employed is 2-methoxy 5-sulfamido benzoic acid.

3. The process of producing a 2,5-disubstituted benzamide in accordance with claim 1 in which the 2,5-disubstituted benzoic acid employed is 2-methoxy 5-methylsulfonylbenzoic acid.

4. The process of producing a 2,5-disubstituted benzamide in accordance with claim 1 in which the 2,5-disubstituted benzoic acid employed is 2-methoxy 5-ethylsulfonylbenzoic acid.

5. The process of producing a 2,5-disubstituted benzamide in accordance with claim 1 in which the amine employed is N,N-diethylethylenediamine.

* * * * *